US012778743B2

(12) United States Patent
Sinha et al.

(10) Patent No.: US 12,778,743 B2
(45) Date of Patent: Nov. 3, 2026

(54) SYSTEM FOR ATTACHING INTRAOCULAR DEVICES TO IRIS TISSUE

(71) Applicant: VERILY LIFE SCIENCES LLC, Dallas, TX (US)

(72) Inventors: Supriyo Sinha, Menlo Park, CA (US); Gregory Arcenio, Redwood City, CA (US); Oleg Rumyantsev, St. Johns, FL (US); Dimitri Azar, Chicago, IL (US); Jeremy Chan, San Jose, CA (US)

(73) Assignee: Verily Health Inc., Dallas, TX (US)

( * ) Notice: Subject to any disclaimer, the term of this patent is extended or adjusted under 35 U.S.C. 154(b) by 403 days.

(21) Appl. No.: 18/540,483

(22) Filed: Dec. 14, 2023

(65) Prior Publication Data

US 2025/0195207 A1 Jun. 19, 2025

(51) Int. Cl.
*A61F 2/14* (2006.01)

(52) U.S. Cl.
CPC ...... *A61F 2/148* (2013.01); *A61F 2220/0016* (2013.01)

(58) Field of Classification Search
CPC ........ A61F 2/16; A61F 2/1635; A61F 2/1648; A61F 2002/169; A61F 2002/1682; A61F 9/00781; A61F 2/1613; A61F 2002/1681; A61F 2002/1689; A61F 2220/0016; A61F 9/0017; A61F 2250/006; A61F 2250/0008; A61F 2/1645; A61F 2/16015; A61F 2/167; A61F 2/1672; A61F 2002/16903; A61F 2/14; A61F 2/141; A61F 2/1602; A61F 2/1605
See application file for complete search history.

(56) References Cited

U.S. PATENT DOCUMENTS

| | | | | |
|---|---|---|---|---|
| 6,197,058 | B1 * | 3/2001 | Portney | A61F 2/1602 623/6.34 |
| 6,554,860 | B2 * | 4/2003 | Hoffmann | A61F 2/1602 623/6.43 |
| 6,981,958 | B1 | 1/2006 | Gharib et al. | |
| 12,496,186 | B1 * | 12/2025 | Aharoni | A61B 17/06166 |

(Continued)

FOREIGN PATENT DOCUMENTS

| | | | | |
|---|---|---|---|---|
| AU | 2014318581 A1 * | 1/2016 | | C08K 5/005 |
| CA | 2908298 A1 * | 1/2008 | | A61B 17/30 |

(Continued)

OTHER PUBLICATIONS

International Search Report and Written Opinion of the International Search Authority for PCT/US2023/084431, issued July 3, 3024, 13 pages.

(Continued)

*Primary Examiner* — Seema Mathew
(74) *Attorney, Agent, or Firm* — Christensen O'Connor Johnson Kindness PLLC

(57) ABSTRACT

An intraocular implant and system comprising: an intraocular device coupled to an attachment mechanism operable to transition between a first configuration and a second configuration to secure the intraocular device to the eye; and a delivery device operable to deliver the intraocular device to the eye and manipulate the attachment mechanism to transition between the first configuration and the second configuration.

17 Claims, 6 Drawing Sheets

(56) References Cited

U.S. PATENT DOCUMENTS

| | | | | |
|---|---|---|---|---|
| 2011/0029075 | A1* | 2/2011 | Willis | A61F 2/1602<br>623/6.43 |
| 2014/0107459 | A1* | 4/2014 | Lind | A61B 3/16<br>600/398 |
| 2022/0183819 | A1* | 6/2022 | Mueller | A61F 2/16 |
| 2023/0363890 | A1* | 11/2023 | Biemold | A61F 2/1664 |
| 2024/0081974 | A1* | 3/2024 | Scalorbi | A61F 2/16 |
| 2024/0335278 | A1* | 10/2024 | Li | A61F 2/1624 |
| 2025/0195207 | A1* | 6/2025 | Sinha | A61B 5/6821 |
| 2026/0047921 | A1* | 2/2026 | Shmukler | A61F 2/16 |

FOREIGN PATENT DOCUMENTS

| | | | | | |
|---|---|---|---|---|---|
| CN | 102970942 | A | * | 3/2013 | A61F 2/14 |
| CN | 216365421 | U | * | 4/2022 | |
| EP | 1862147 | A1 | * | 12/2007 | A61F 2/1613 |
| FR | 2998474 | A1 | * | 5/2014 | A61F 2/161 |
| WO | WO-2015148673 | A1 | * | 10/2015 | A61F 9/0026 |
| WO | 2016004223 | A1 | | 1/2016 | |
| WO | 2018078026 | A1 | | 5/2018 | |
| WO | 2022035889 | A1 | | 2/2022 | |

OTHER PUBLICATIONS

T. Choragiewicz, et al.; "Outcomes of Sutureless Iris-Claw Lens Implantation;" Hindawi Publishing Corporation; Journal of Ophthalmology; vol. 2016; Article ID 7013709; 1-7 pps.; http://dx.doi.org/10.1155/2016/7013709.

* cited by examiner

SYSTEM FOR ATTACHING INTRAOCULAR DEVICES TO IRIS TISSUE

FIELD

The subject matter of this disclosure relates to techniques for attaching intraocular devices to the eye, and more specifically intraocular devices coupled to attachment mechanisms for attaching the devices to iris tissue.

BACKGROUND

The implantation of intraocular devices inside of the eye using minimally invasive surgical methods is often very challenging. In some aspects, intraocular devices include barbs or rely on the inherent structural properties of the ocular tissue at the implantation site to hold the devices in place. When a precise positioning (e.g., both lateral and angular) of the intraocular implant within the eye is required, however, barbs may not be suitable. In addition, the manufacture of three-dimensional features like barbs can be expensive or infeasible when the device size is so small (e.g., on the order of 1 mm or less).

SUMMARY

An aspect of the disclosure is directed to systems and techniques for attaching intraocular devices to the eye, and more specifically the iris of the eye. For example, in some aspects, the intraocular device may be, or may otherwise include, an intraocular pressure sensor that is implanted in the eye and measures a pressure within the eye. Such devices may require precise lateral and angular alignment within the eye so that the measurements they obtain can be properly read by an external reading device. It is therefore important that the implanted device be able to maintain its position within the eye. In addition, it is desirable that implantation of the device be achieved using minimally invasive surgical methods, which can also be challenging. Thus, a minimally invasive delivery system for delivery and attaching the intraocular device to the iris is further disclosed.

Representatively, in one aspect, an intraocular implant includes an intraocular device operable to detect a characteristic of an eye; and an attachment mechanism coupled to the intraocular device, the attachment mechanism operable to transition between a first configuration and a second configuration to secure the intraocular device to the eye. In some aspects, the intraocular device includes an intraocular pressure sensor. In some aspects, the attachment mechanism includes a deployable leg. In some aspects, the deployable leg transitions between the first configuration in which the deployable leg is compressed and the second configuration in which the deployable leg is extended to secure the intraocular device to an iris of the eye. In some aspects, the deployable leg includes a torsional spring that rotates along an axis during the transition to the second configuration to thread the leg through the iris. In still further aspects, the intraocular device and the attachment mechanism are coplanar. The attachment mechanism may include a planar substrate having a first gripping portion and a second gripping portion that open to define a gap in the first configuration and close to grip a tissue within the gap in the second configuration to secure the intraocular device to the eye. In some aspects, the first gripping portion and the second gripping portion move within a plane of the device to open and close the gap. In still further aspects, the first gripping portion and the second gripping portion are a first pair of gripping portions, and the attachment mechanism further comprises a second pair of gripping portions having a first gripping portion and a second gripping portion. In some aspects, the attachment mechanism includes a first structure extending form one side of the body portion and operable to be inserted into a tissue of the eye and a second structure extending from an opposite side of the body portion and operable to be inserted into the tissue of the eye. The first structure may be a beveled blade edge. The second structure may be a different structure than the first structure.

In another aspect, an intraocular implant system includes an intraocular device coupled to an attachment mechanism operable to transition between a first configuration and a second configuration to secure the intraocular device to the eye; and a delivery device operable to deliver the intraocular device to the eye and manipulate the attachment mechanism to transition between the first configuration and the second configuration. In some aspects, the intraocular device includes an intraocular pressure sensor. In some aspects, the attachment mechanism comprises a deployable portion that is manipulated by the delivery device to transition between the first configuration in which the deployable portion is compressed and the second configuration in which the deployable portion is extended to secure the intraocular device to an iris of the eye. The deployable portion may include a torsional spring and a hooked end that rotates along an axis during the transition to the second configuration to thread the hooked end through the iris. The intraocular device and the attachment mechanism may be coplanar. In some aspects, the attachment mechanism may include a planar substrate having a first gripping portion and a second gripping portion that are manipulated by the delivery device to open to define a gap in the first configuration and close to grip a tissue within the gap in the second configuration to secure the intraocular device to the eye. In some aspects, the attachment mechanism includes a first structure operable to be inserted into a tissue of the eye and a second structure different from the first structure that is operable to be inserted into the tissue of the eye. In still further aspects, at least one of the first structure or the second structure comprises a beveled blade.

The above summary does not include an exhaustive list of all aspects of the present disclosure. It is contemplated that the disclosure includes all systems and methods that can be practiced from all suitable combinations of the various aspects summarized above, as well as those disclosed in the Detailed Description below and particularly pointed out in the Claims section. Such combinations may have particular advantages not specifically recited in the above summary.

BRIEF DESCRIPTION OF THE DRAWINGS

Several aspects of the disclosure here are illustrated by way of example and not by way of limitation in the figures of the accompanying drawings, in which like references indicate similar elements. It should be noted that references to "an" or "one" aspect in this disclosure are not necessarily to the same aspect, and they mean at least one. Also, in the interest of conciseness and reducing the total number of figures, a given figure may be used to illustrate the features of more than one aspect of the disclosure, and not all elements in the figure may be required for a given aspect.

DETAILED DESCRIPTION

Several aspects of the disclosure with reference to the appended drawings are now explained. Whenever the shapes, relative positions and other aspects of the parts described are not explicitly defined, the scope of the invention is not limited only to the parts shown, which are meant merely for the purpose of illustration. Also, while numerous details are set forth, it is understood that some aspects of the disclosure may be practiced without these details. In other instances, well-known circuits, structures, and techniques have not been shown in detail so as not to obscure the understanding of this description.

The terminology used herein is for the purpose of describing particular aspects only and is not intended to be limiting of the disclosure. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

Figure 1:
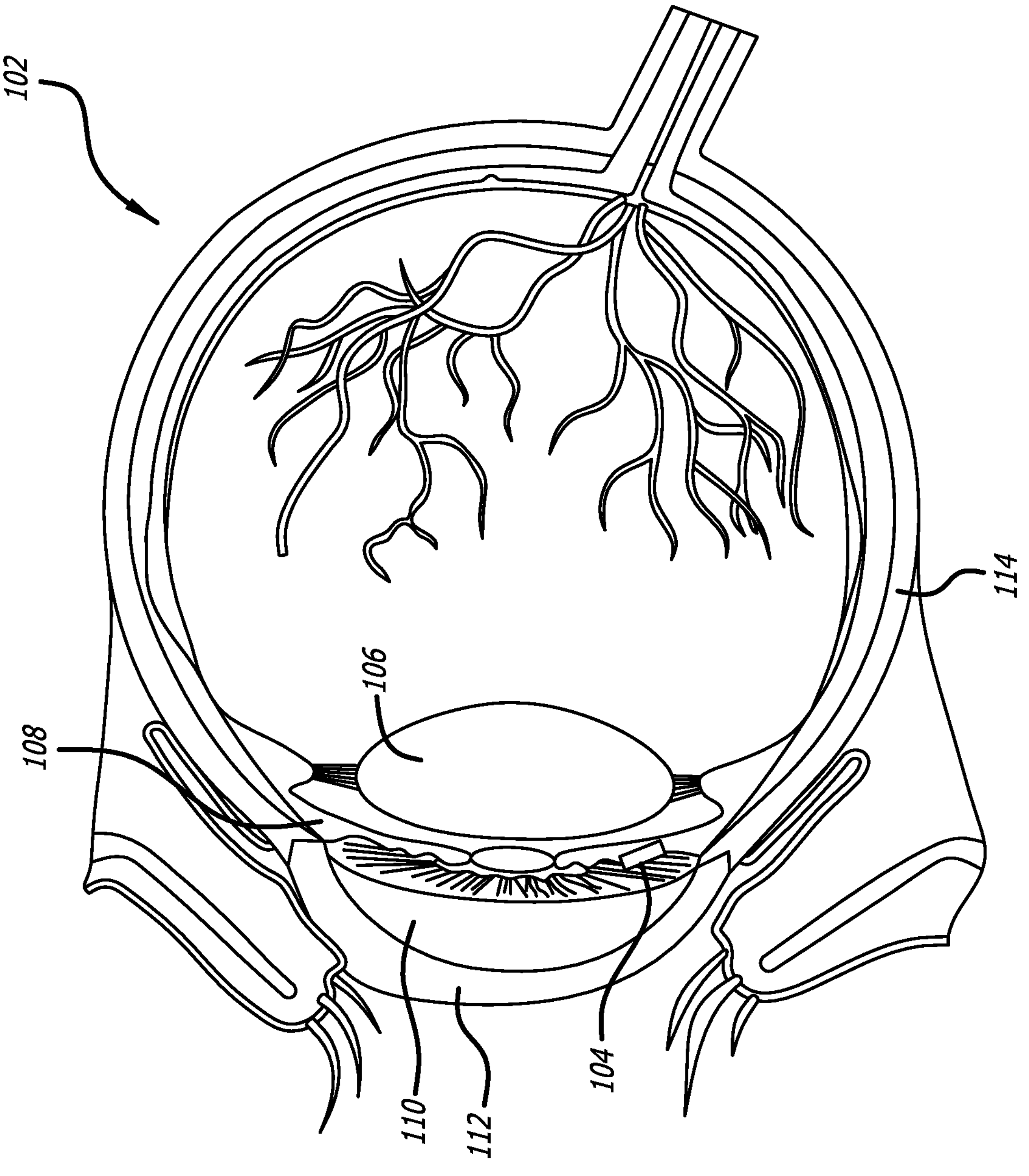
FIG. 1 shows a schematic illustration of an example system including an intraocular implant in an eye.

FIG. 1 shows an example eye 102 having an intraocular implant 104 (e.g., an intraocular pressure sensor) implanted thereon. Representatively, as can be understood from FIG. 1, eye 102 may include lens 106, which sits behind the iris 108, and cornea 112, which sits in front of the iris 108. Cornea 112 is separated from lens 106 by anterior chamber 110. The sclera 114 is further shown supporting the eyeball and continuous with cornea 112. FIG. 1 further shows implant 104 attached to iris 108. While the drawings in this disclosure may not be to scale, they do illustrate that implant 104 is small enough (e.g., about 0.25-0.5 mm thick and/or about 1 mm diameter) to be implanted on iris 108. Implant 104 may include an active or passive sensor or device. For example, in some aspects, implant 104 includes an active device that has a source of power and/or can transmit signals containing information about the eye characteristic (e.g., an intraocular pressure (IOP)), to an external reader. In other aspects, implant may include a passive device that does not have a source of stored power that is used to transmit a signal containing information about a characteristic of the eye, for example an intraocular pressure (IOP). Instead, a part of implant 104 may be designed to bend or compress or conform according to the IOP, and that part is also designed to reflect incident optical energy. As a result, implant 104 changes how it reflects the optical energy, as a function of the IOP at that moment. Thus, the reflection changes in that it follows the changing IOP (in the anterior chamber), for example over the course of a day. As previously discussed, the device may be small and thin so as to be implanted or attached to the iris in a minimally invasive manner, more easily and with less risk of complications as compared to implant locations that are further inside the eye. For example, the implant can be made sufficiently small, e.g., having a footprint or area in the x-y plane of about 1 $mm^2$ and a thickness in the z direction of 0.2 to 0.3 mm.

Figure 2:
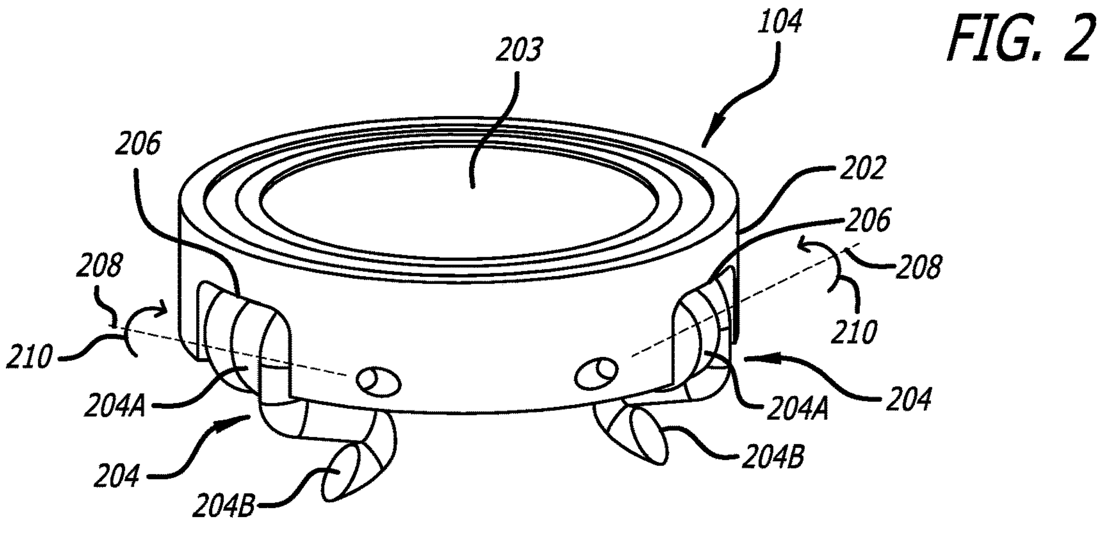
FIG. 2 shows a perspective view of an implant of FIG. 1 in a non-deployed configuration.
Figure 3:
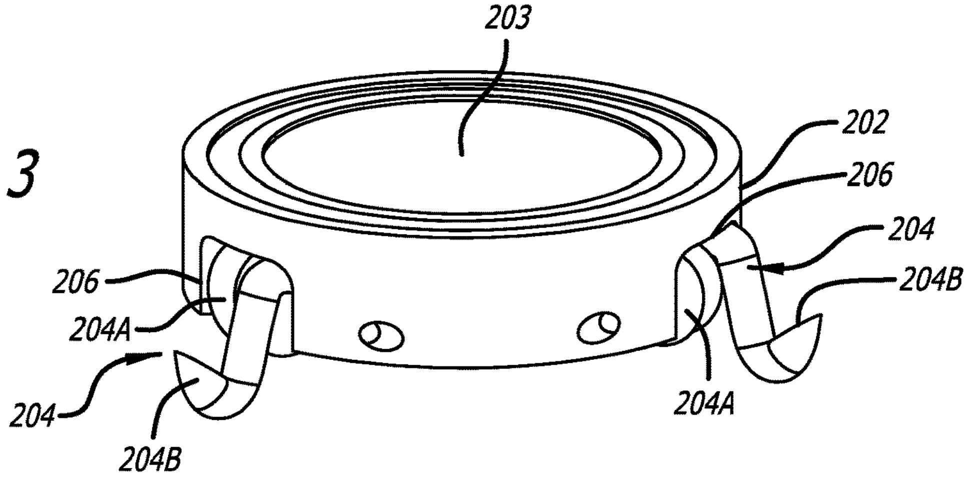
FIG. 3 shows a perspective view of an implant of FIG. 1 in a deployed configuration.

FIGS. 2-3 illustrates perspective views of one aspect of an intraocular implant in a non-deployed configuration (FIG. 2) and a deployed configuration (FIG. 3) in which implant can attach to the eye tissue. Representatively, intraocular implant 104 may be implanted or otherwise attached to an iris of the eye as previously discussed in reference to FIG. 1. From this view, it can be seen that implant 104 includes a body portion 202 which may be, or otherwise contain, an intraocular device 203 such as a sensor or other mechanism for detecting a characteristic (e.g., IOP) of the eye. Body portion 202 may, for example, be a housing, module or other type of enclosure that contains device 203 and is further coupled to one or more of an attachment assembly or mechanism 204. Attachment mechanism 204 is used to attach or secure implant 204 to the eye at a precise lateral and angular alignment within the eye so that the measurements can be properly read by an external reading device. In this aspect, attachment mechanism 204 may be a deployable leg made up of a spring 204A and hook like end 204B. The spring 204A may, for example, be a torsion spring that is fixedly attached to body portion 202 at one end and has an opposite free end that extends outside the body portion to form the hook like end 204B. For example, spring 204A may be positioned within a compartment, chamber or recessed region 206 formed in body portion 202. Hook like end 204B may have the shape of a "J" or other similar hook like shape and extend outside of the recessed region 206. In this aspect, in the non-deployed, retracted or compressed configuration shown in FIG. 2, spring 204A is compressed and hook like end 204B is positioned below body portion 202. In this configuration, hook like end 204B is facing downward and can pierce through the underlying tissue. To transition to the deployed or extended configuration shown in FIG. 3, spring 204A may be rotated around its axis 208 as shown by arrow 210. This, in turn, expands or extends spring 204A so that hook like end 204B extends out of the recessed region 206 and rotates upward as shown in FIG. 3. Rotation of end 204B upward as shown causes end 204B to then hook into the tissue and securely embed implant 104 into the underlying tissue (e.g., the iris). In some aspects, each of the attachment mechanisms 204 may transition between one configuration (e.g., non-deployed configuration or position) to another configuration (e.g., deployed configuration or position) simultaneously or at the same time. In other aspects, each attachment mechanism 204 may transition between non-deployed and deployed configurations or positions at different times as desired.

Figure 4:
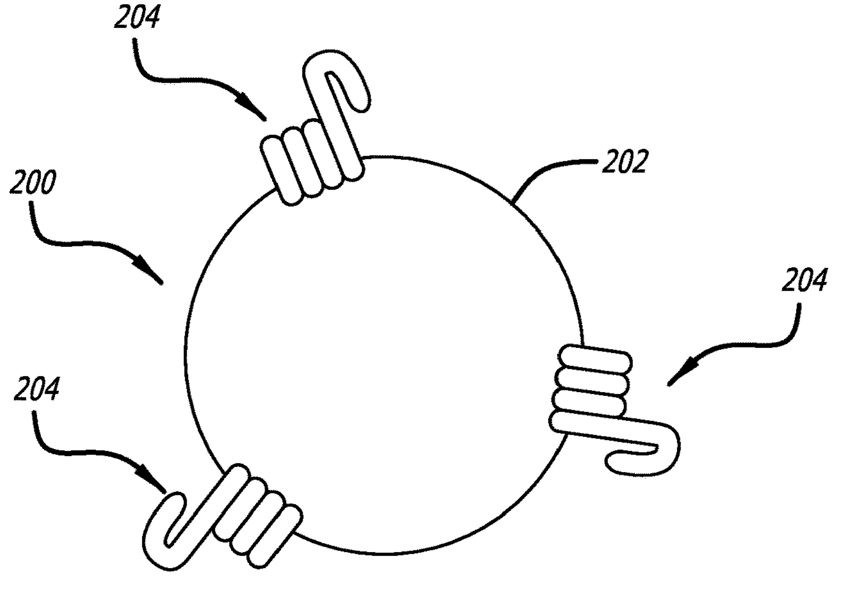
FIG. 4 shows a top bottom plan view of the implant of FIGS. 2-3.

It should further be understood that although in the view shown in FIGS. 2-3 only two attachment mechanisms 204 are visible, it is contemplated that implant 104 may include more or fewer attachment mechanisms 204. Representatively, in some aspects, implant 104 may include three or more attachment mechanisms 204 evenly spaced around implant 104. Representatively, FIG. 4 illustrates a bottom view of implant 104 of FIGS. 2-3 in which all three attachment mechanisms 204 can be seen evenly spaced around implant 104. Each of attachment mechanisms 204 may transition between the non-deployed and deployed configurations at a same or different times as previously discussed. In addition, torsion springs 204A may be made from any one of a variety of biocompatible stainless steel spring materials suitable for medical devices. Moreover, in some aspects, nitinol (NiTi) may be used as the material for manufacturing the torsion springs. One advantage of using NiTi would be its superelasticity which could potentially improve the range of motion of the deployable legs and reduce possible permanent deformation prior to final deployment.

Figure 5A:
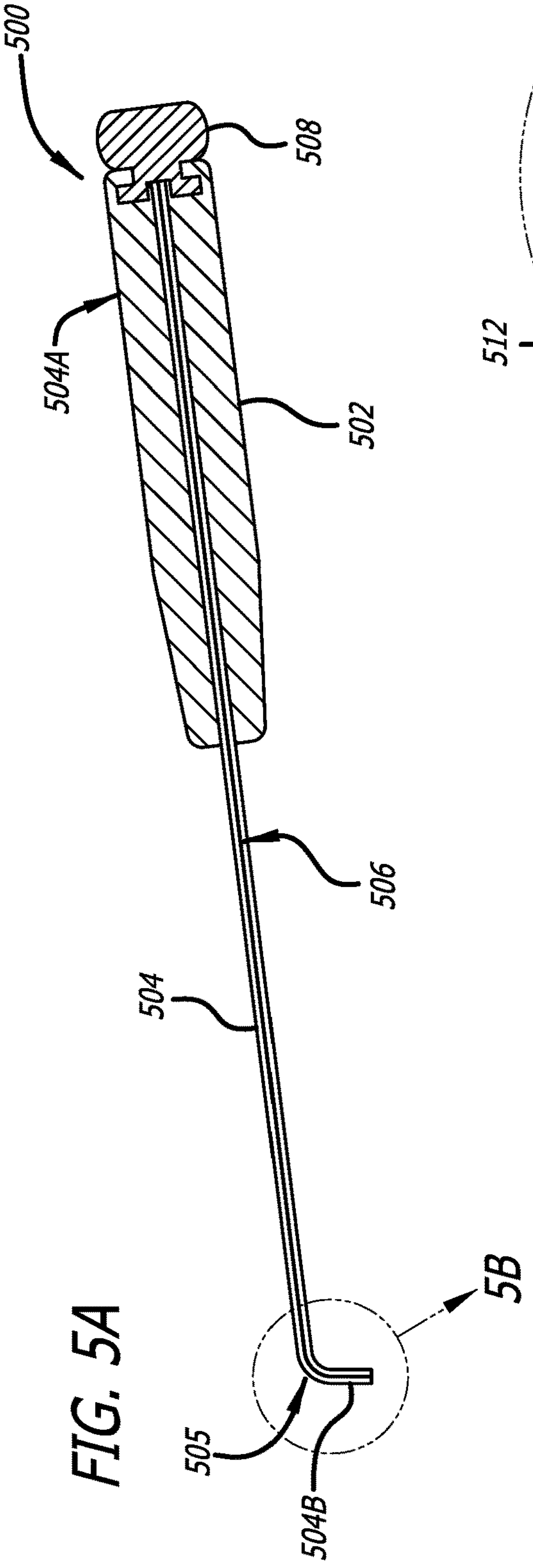
FIG. 5A shows a cross-sectional side view of a delivery device for implanting an intraocular implant in an eye.

Referring now to FIGS. 5A-7, FIGS. 5A-7 illustrate aspects of one exemplary delivery device for attaching an implant to the surface of the eye. Representatively, FIG. 5A illustrates a cross-sectional side view of delivery device 500 having implant 104 loaded therein for delivery and implantation on the eye. From this view, it can be seen that delivery device 500 may include a handle 502 connected to a shaft 504. Shaft 504 may have a proximal portion or end 504A that is attached to handle 502 and remains external to the eye during implantation, and a distal portion or end 504B that is inserted into the eye and contacts the eye tissue (e.g., the iris) during implantation. In this aspect, shaft 504 may be a relatively rigid and straight tube that includes a bend or curve 505 of approximately ninety degrees at the distal portion or end 504B to help with insertion and positioning of the distal portion or end 504B on the eye tissue. Shaft 504 may further include a hollow channel that receives a translating rod 506 and implant 104. Translating rod 506 extends from proximal portion or end 504A of shaft 504 to the implant 104 positioned at the distal portion or end 504B of shaft 504. In some aspects, handle 502 may further include a rotatable end 508 attached to the proximal end of translating rod 506 that can be used to manipulate translating rod 506 within shaft 504 and deploy the implant 102.

Figure 5B:
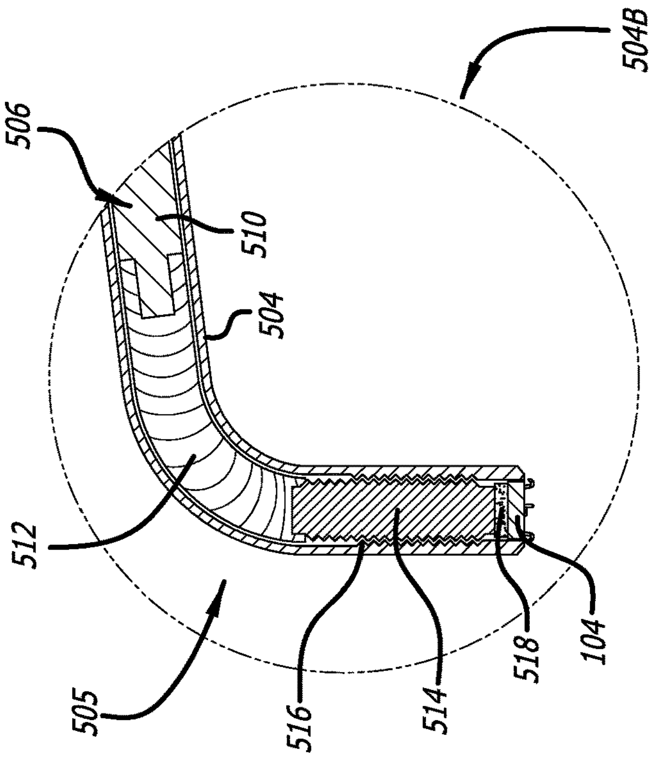
FIG. 5B shows a cross-sectional magnified cross-sectional view of a portion of the delivery device of FIG. 5A.

Representatively, as can be seen from the magnified view of the distal end 504B shown in FIG. 5B, translating rod 506 may include a portion 510 that extends from the proximal to distal end 504A-B of shaft 504. One end of portion 510 connects to the rotatable handle end 508. The other end of portion 510 connects to a relatively flexible portion 512 that can bend and conform to the shape of the curved portion 505 of shaft 504. For example, flexible portion 512 may be made of a spring like structure that can bend as shown. Flexible portion 512 is further connected to a threaded portion 514. Threaded portion 514 may be a relatively rigid structure (e.g., a screw like structure) that is aligned with a complimentary threaded portion 516 formed along an interior surface of distal end 504B of shaft 504. In this aspect, a rotation of threaded portion 514 within shaft 504 translates the distal portion or end of rod 506 up and/or down shaft 504 depending on the direction of rotation. Distal to threaded portion 514 is an implant receiving portion 516. Implant receiving portion 516 may be a disk or other similarly shaped member that is positioned between the threaded portion 516 and implant 104 loaded into the distal end 504B of shaft 504. Implant receiving portion 516 may, in some aspects, be a compliant or gripping like structure that can help to transmit the motion of the threaded portion 514 to the implant 104 to transition the implant between non-deployed/deployed configurations and secure the implant to the tissue.

Figure 6:
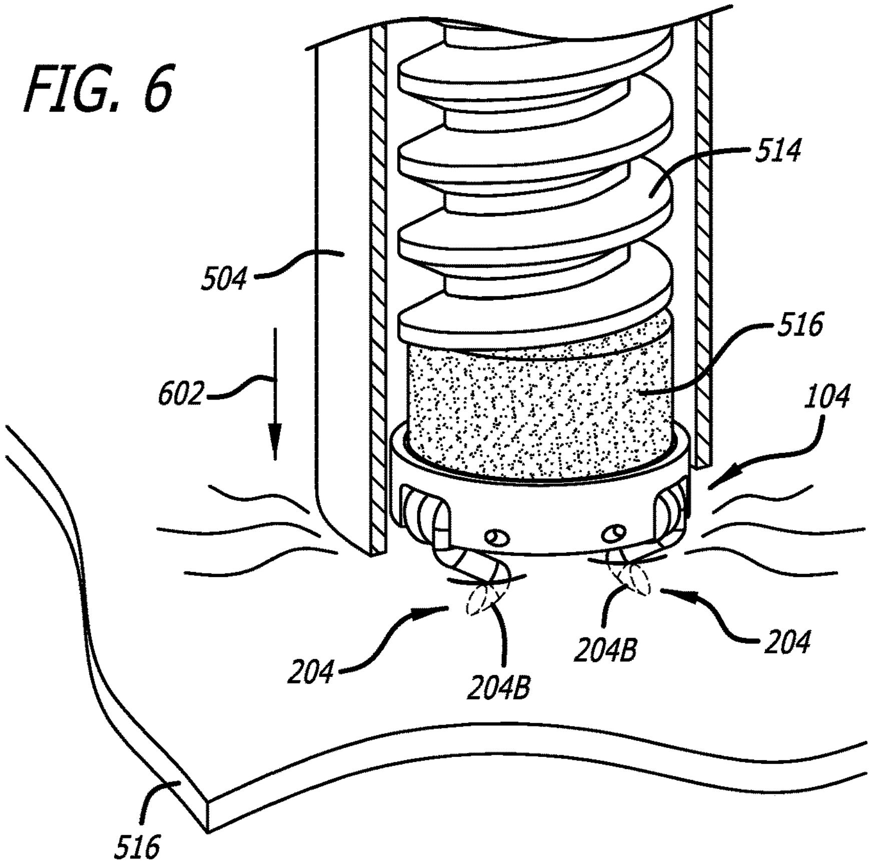
FIG. 6 shows a magnified perspective view of a portion of the delivery device of FIG. 5A with the implant in a non-deployed configuration.
Figure 7:
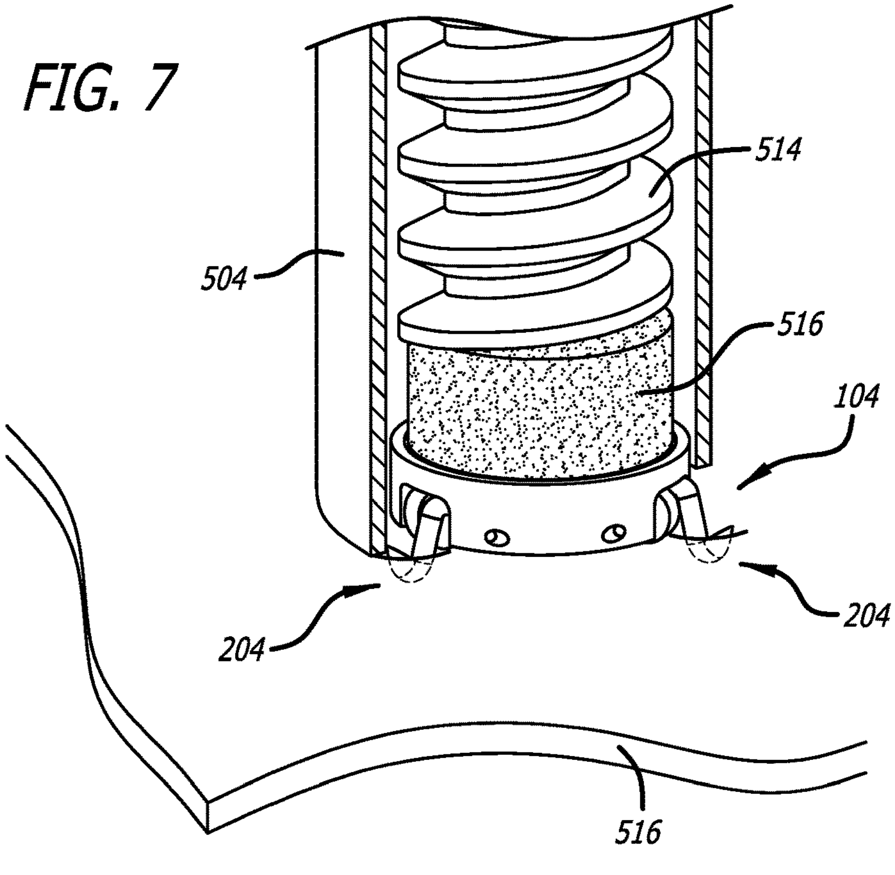
FIG. 7 shows a magnified perspective view of a portion of the delivery device of FIG. 5A with the implant in a deployed configuration.

Representatively, prior to insertion into the eye, implant 104 is loaded into distal end 504A of shaft 504 as shown in FIG. 5B. The spring and hook like ends of the attachment mechanisms 204 are compressed into the non-deployed configuration shown in FIG. 2. With attachment mechanisms 204 compressed, implant 104 can be pushed into the distal end 504B of shaft 504. The inner walls of shaft 504 serve to keep the attachment mechanisms 204 in the compressed configuration prior to deployment. Likewise, the outward, radially-directed force exerted by the compressed torsional springs serves to keep implant 104 mounted within the distal end 504B of shaft 504. At the time of implantation, the distal end 504B of shaft 504 is inserted through an incision in the cornea and placed onto the surface of the iris at the desired implant location. In doing so, the bottom of implant 104 is pressed against the iris such that the beveled tips of the hook like ends 204B of the attachment mechanisms 204 embed themselves into the surface of the iris 516, as shown in FIG. 6. Translating rod 506 can then be used to push implant 104 out of shaft 504. Representatively, the surgeon can rotate the rotatable end 508 of handle 502, which in turn, rotates the threaded portion 514 of translating rod 506. The rotation of the threaded portion 514 of rod 506 along the complimentary threading 516 translates rod 506 through shaft 504 in the direction of arrow 602. This, in turn, pushes implant 104 out of the distal end 504B of shaft 504 and further presses implant 104 into tissue 516. Once implant 104 is pushed out of the distal end 504B of shaft 504, the deployable attachment mechanisms 204 cease to be constrained by the inner walls of shaft 504. The active ends 204B of the torsion springs 204A are therefore free to rotate through their prescribed arc of motion to the deployed configuration. FIG. 7 shows implant 104 pushed out of shaft 504 and in the deployed configuration with ends 204B fully extended. The motion of each of ends 204B may be in an arc that results in the sharp tips or ends 204B becoming fully embedded into the iris tissue. In this way, implant 104 is pulled downward onto the surface of the iris and secured in place at the precise positioning (both lateral and angular) through the threading of each attachment mechanism 204 into the tissue. Once implant 104 is secured in place, the surgeon removes device 500 from the eye leaving behind the implant 104.

Figure 8:
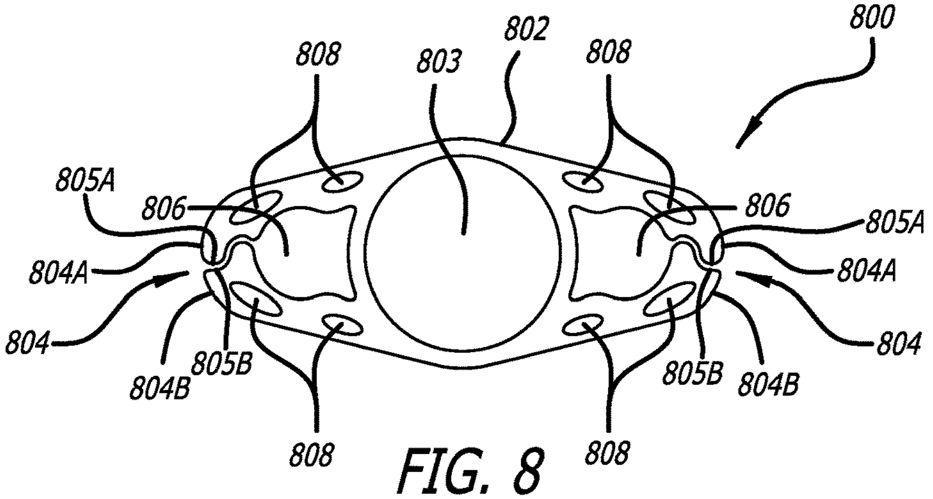
FIG. 8 illustrates a top plan view of another aspect of an implant.
Figure 9:
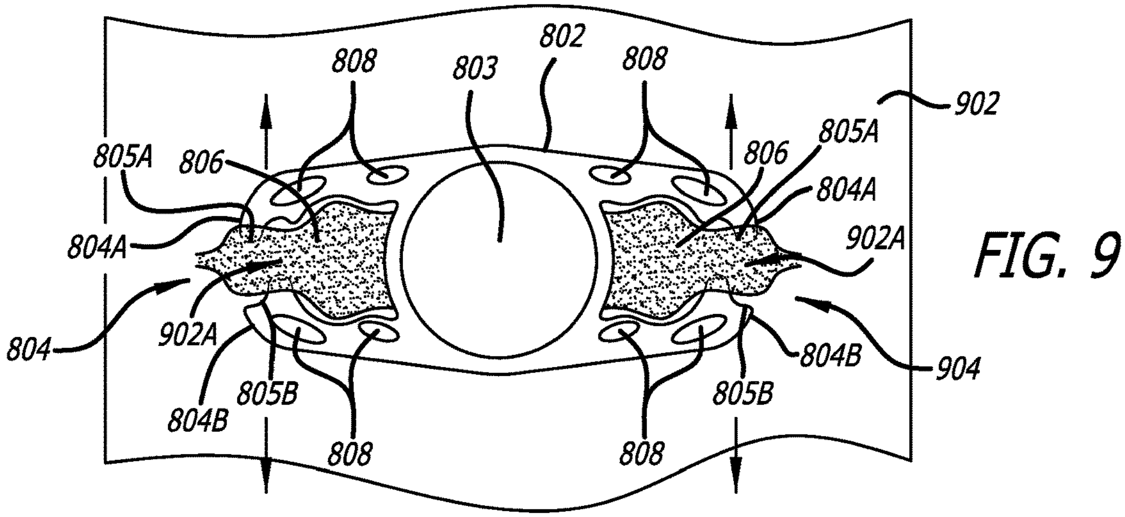
FIG. 9 illustrates a top plan view of the implant of FIG. 8 in one configuration.
Figure 10:
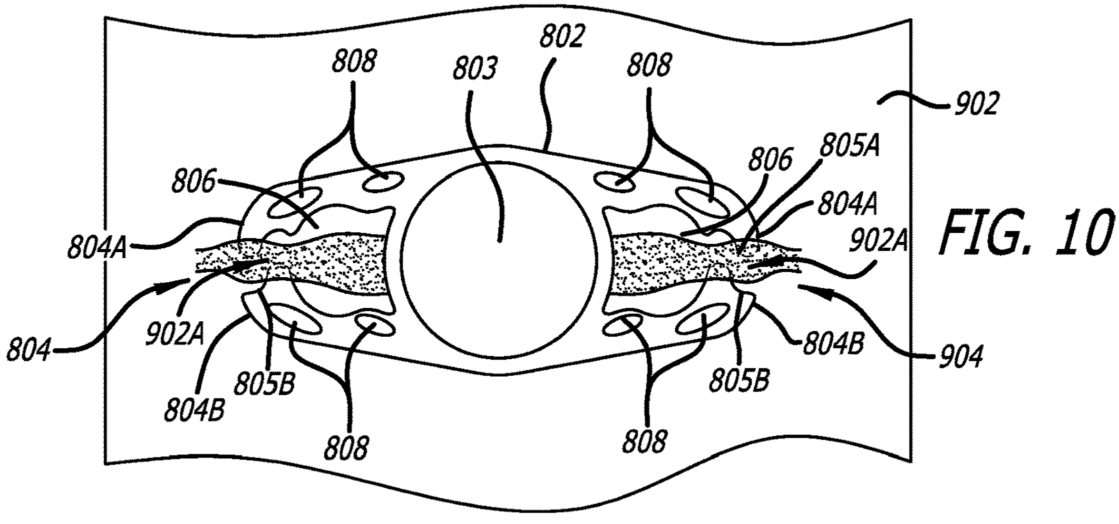
FIG. 10 illustrates a top plan view of the implant of FIG. 9 in another configuration.

Referring now to FIGS. 8-10, FIGS. 8-10 illustrates an alternative intraocular implant. Representatively, FIG. 8-10 illustrate top plan views of a substantially planar intraocular implant 800 that may be attached to the eye. Similar to the previously discussed implant, implant 800 may include a body portion 802 which may be, or otherwise contain, an intraocular device 803 such as a sensor or other mechanism for detecting a characteristic (e.g., IOP) of the eye. Body portion 802 may, for example, be considered a module, housing or other type of enclosure or structure that contains or otherwise supports device 803 and is further coupled to one or more of an attachment assembly or mechanism 804. Similar to the previously discussed attachment mechanisms, attachment mechanism 804 is used to attach or secure implant 800 to the eye at a precise lateral and angular alignment within the eye so that the measurements can be properly read by an external reading device. In this aspect, however, attachment mechanism 804 and body portion 802 may be substantially coplanar such that implant 800 has a full planar geometry. For example, in some aspects, implant 800 could be formed from a substrate that is laser cut or made through a micro electrical discharge machining (EDM) process with the desired features (e.g., body portion 802 and attachment mechanism 804). Several mechanical features can be included in implant 800 to facilitate adjustment of the force required to transition attachment mechanism 804 between open and closed configurations. Additionally, these features could also enable the utilization of brittle materials such as glass as the substrate for device 803 and/or body portion 804. In some aspects, the substrate used to form body portion 804 could be made from the same material as the active device 803 (e.g., glass or silicon for an intraocular pressure sensor). In still further aspects, a frame could be attached to, or embedded within, the device to provide resistance to substrate material fracture. Epoxies and other materials could also be used to coat or to overmold the device to prevent surface cracking. Moreover, holes can be patterned into the device to allow for (delivery and recovery) tool insertion. For example, a nitinol hook could be used to apply an out of plane force to the device to pull gripping portions of the attachment mechanism 804 apart. These holes could be patterned in a keyhole fashion to allow for easy detachment from the delivery tool after implantation. In some aspects, spreading jaws can be used as well to push portions of attachment mechanism 804 apart within the plane of the device.

Representatively, body portion 802 may be formed at a center of implant 800 and attachment mechanism 804 may be formed and extend radially outward from opposite sides of body portion 802. Attachment mechanism 804 may be made up of a first gripping portion 804A and a second gripping portion 804B that operate like teeth or a similar clamping mechanism to grip tissue. For example, first and second gripping portions 804A-B can be opened (e.g., spaced apart) and closed (e.g., moved together) relative to one another to grip or clamp onto tissue and hold implant 800 in place. In some aspects, a tool opening 806 may be formed between each of gripping portions 804A-B and body portion 802 to facilitate opening and closing of gripping portions 804A-B using a delivery tool as will be described in more detail in reference to FIGS. 9-11. Additional openings 808 may also be formed around tool opening 806 that can receive additional portions of the delivery tool to help open/close portions 804A-B of attachment mechanism 804 or to optimize mechanical properties of implant 800. In some aspects, tool opening 806 may be a relatively large opening suitable for receiving a portion of the delivery tool that can be used to manipulate implant 800 between configurations (e.g., open/non-deployed configuration and closed/deployed configuration). In some aspects, tool opening 806 may have a bell like shape. Additional openings 808 may be smaller than tool opening 806 and, in some cases elongated, such that they are formed in the remaining implant material around tool opening 806 and gripping portions 804A-B.

Referring now in more detail to gripping portions 804A-B, in some aspects, first gripping portion and second gripping portion 804A, 804B may have interfacing edges 805A and 805B that have jagged, tooth like, serpent or curved shapes that are complimentary to one another. Interfacing edges 805A and 805B are together or near one another in the closed configuration shown in FIG. 8 and can be moved away from one another to an open configuration as shown in FIG. 9 such that a tissue receiving gap 904 is formed between them. First and second gripping portions 804A-B may be biased toward one another and/or to the closed position in the absence of an external force. To move portions 804A-B away from one another, an external force may be used. For example, a portion of the delivery tool may be inserted into tool openings 806 between each of first and second gripping portions 804A-B and used to separate first and second gripping portions 804A-B in the direction of the arrows. This, in turn, creates a gap 904 that receives a portion 902A of tissue 902 as shown in FIG. 9. Removal of the portion of the delivery tool then allows first and second gripping portions 804A-B to move back toward one another and edges 805A-B grip or clamp onto the tissue portion 902A pinched in between as shown in FIG. 10. This, in turn, holds implant 800 at the desired position on tissue 902.

Figure 11:
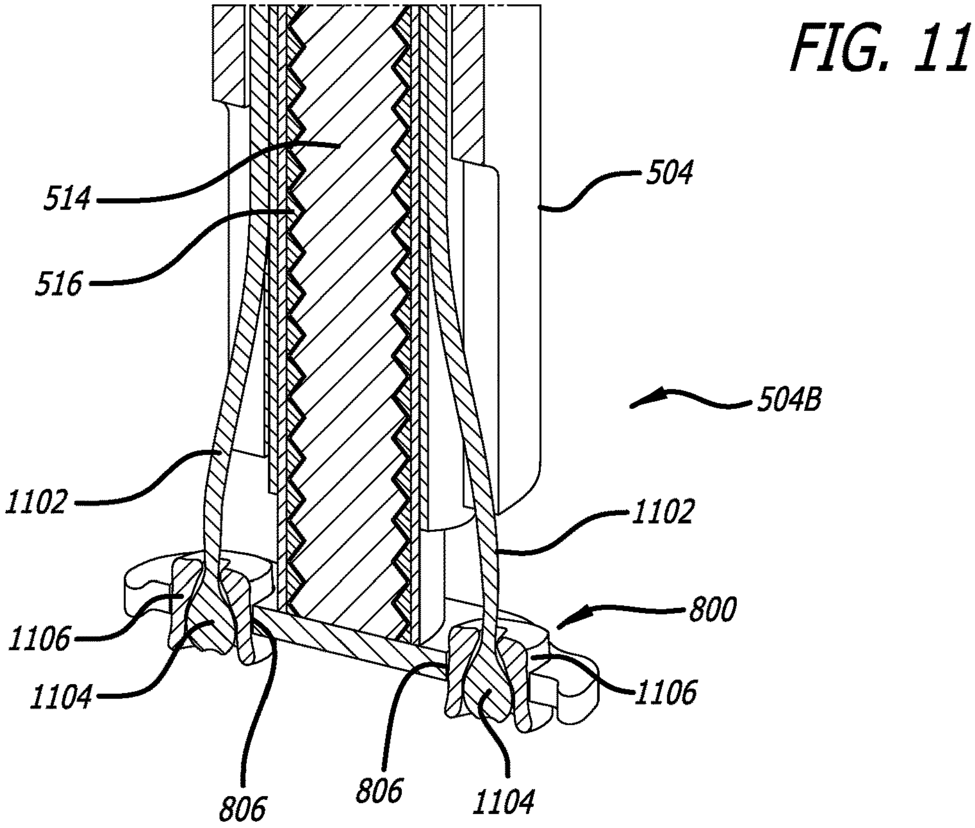
FIG. 11 illustrates a magnified perspective view of a portion of the delivery device of FIG. 5A configured for delivering the implant of FIG. 8.

FIG. 11 shows a cross-sectional perspective view of one representative delivery tool that may be used to deliver implant 800 to the desired tissue. Representatively, FIG. 11 may be understood as illustrating a magnified cross-sectional view of the distal portion 504B of delivery tool 500 as described in reference to FIG. 5A-5B. Delivery tool 500 may therefore include the same aspects as described in reference to FIG. 5A-5B and operate in the same manner. In this configuration, however, the distal end 504B of delivery tool may also include arms 1102 having wedge elements 1104, 1106 that can be inserted into tool openings 806 to spread attachment mechanisms 804 apart. In this aspect, arms 1102 can extend from the distal end of shaft 504 of delivery tool 500. During device deployment, wedge elements 1104, 1106 may be simultaneously pulled in the proximal direction via a spooling knob attached to the tool handle (e.g., handle 502). As the wedge elements 1104, 1106 are pulled through openings 806 of implant 800, gripping portions 804A-B are forced to spread slightly apart. While this is happening, implant 800 is biased onto the iris surface to promote billowing of the iris tissue within gap 904 between gripping portions 804A-B. Continued actuation of the deployment tool 500 results in wedge elements 1104, 1106 being pulled completely out of implant 800 which in turn causes gripping portions 804A-B to close down on any iris tissue that has billowed between gripping portions 804A-B thereby securing the device to the iris as shown in FIG. 10.

Figure 12:
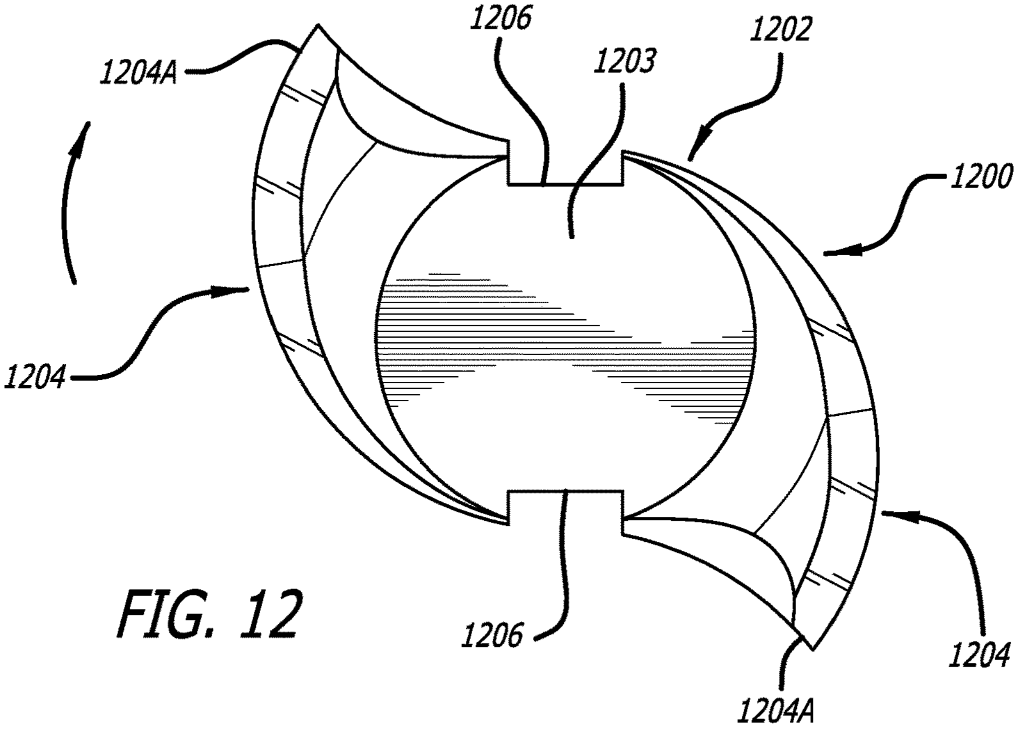
FIG. 12 illustrates a top plan view of another aspect of an implant.

Referring now to FIG. 12, FIG. 12 illustrates an alternative implant configuration with a full planar geometry. Implant 1200 is similar to the previously discussed implant 800 and includes substantially planar body portion 1202 and attachment mechanism 1204. For example, implant 1200 may be formed from a substrate by laser cutting the substrate or through a micro electrical discharge machining (EDM)

process with the desired features (e.g., body portion 1202 and attachment mechanism 1204). In addition, similar to the previous implant, body portion 1202 may be formed at a center of implant 1200 and attachment mechanism 1204 may be formed and extend radially outward from opposite sides of body portion 1202. Body portion 1202 may be, or otherwise contain, an intraocular device 1203 such as a sensor or other mechanism for detecting a characteristic (e.g., IOP) of the eye. Body portion 1202 may, for example, be considered a module, housing or other type of enclosure or structure that contains or otherwise supports device 1203 and is further coupled to one or more of an attachment assembly or mechanism 1204. In this configuration, however, attachment mechanism 1204 may include beveled blade edges 1204A that extend radially outward from body portion 1202. Beveled blade edges 1204A may have a substantially triangular shape that has curved edges that are beveled and can be inserted into the tissue at an oblique angle. For example, in some aspects, any one or more of the previously discussed delivery devices may be used to position implant 1200 on the iris tissue at a first configuration. Implant 1200 may then be manipulated to a second configuration in which blade edge 1204A becomes embedded into the tissue. Representatively, implant 1200 may be rotated as illustrated by the arrows so that blade edge 1204A becomes embedded into the tissue at an oblique angle. To achieve implantation, implant 1200 may be inserted into the shaft of the delivery device as previously discussed, and then be pushed out of the shaft (e.g., shaft 504 of delivery device 500) using the previously discussed rod (e.g., translation rod 506). Delivery device 1200 may further include arms (e.g., arms 1102) that can engage the implant at recessed regions 1206 to manipulate implant 1200 as desired. In addition, in some aspects, although both of attachment mechanisms 1204 are shown as beveled edges, in some aspects, attachment mechanisms 1204 could be different structures. For example, one of attachment mechanisms 1204 could be a beveled edge and the other attachment mechanism could be a different structure such as teeth or barb like features that would embed into the tissue to facilitate a secure attachment of implant 1200 to the iris as previously discussed.

While certain aspects have been described and shown in the accompanying drawings, it is to be understood that such are merely illustrative of and not restrictive on the broad invention, and that the invention is not limited to the specific constructions and arrangements shown and described, since various other modifications may occur to those of ordinary skill in the art. For example, it should be understood that while a passive or active implant or sensor is primarily disclosed herein, in some aspects, the implant may be any type of intraocular implant that requires precise positioning in the eye, and could benefit from implantation using the attachment mechanisms and delivery devices disclosed herein. In addition, the aspects disclosed herein are not limited to ophthalmological/medical sensing applications and can be used in a much broader range of measurement applications involving repetitive repositioning of the miniature sensor and an external optical measurement device. The description is thus to be regarded as illustrative instead of limiting.

What is claimed is:

1. An intraocular implant comprising:

an intraocular device operable to detect a characteristic of an eye; and an attachment mechanism coupled to the intraocular device, the attachment mechanism operable to transition between a first configuration and a second configuration to secure the intraocular device to the eye, wherein the attachment mechanism comprises a deployable leg with a torsional spring that rotates about an axis during the transition to the second configuration to thread the leg through the iris.

2. The intraocular implant of claim 1 wherein the intraocular device comprises an intraocular pressure sensor.

3. The intraocular implant of claim 1 wherein the deployable leg transitions between the first configuration in which the deployable leg is compressed and the second configuration in which the deployable leg is extended to secure the intraocular device to an iris of the eye.

4. An intraocular implant comprising:

an intraocular device operable to detect a characteristic of an eye; and an attachment mechanism coupled to the intraocular device, the attachment mechanism operable to transition between a first configuration and a second configuration to secure the intraocular device to the eye, wherein the attachment mechanism comprises a planar substrate having a first gripping portion and a second gripping portion that open to define a gap in the first configuration and close to grip a tissue within the gap in the second configuration to secure the intraocular device to the eye, wherein the attachment mechanism includes one or more tool openings configured to receive a tool that moves the first and second gripping portions away from one another into the first configuration, the first and second gripping portions being biased toward one another such that removal of the tool causes the first and second gripping portions to move toward one another into the second configuration to secure tissue therebetween.

5. The intraocular implant of claim 4 wherein the first gripping portion and the second gripping portion move within a plane of the device to open and close the gap.

6. The intraocular implant of claim 4 wherein the first gripping portion and the second gripping portion are a first pair of gripping portions, and the attachment mechanism further comprises a second pair of gripping portions having a first gripping portion and a second gripping portion.

7. The intraocular implant of claim 4 wherein the attachment mechanism comprises a first structure extending from one side of a body portion and operable to be inserted into a tissue of the eye and a second structure extending from an opposite side of the body portion and operable to be inserted into the tissue of the eye.

8. The intraocular implant of claim 7 wherein the first structure comprises a beveled blade edge.

9. The intraocular implant of claim 7 wherein the second structure comprises a different structure than the first structure.

10. An intraocular implant system comprising:

an intraocular device coupled to an attachment mechanism operable to transition between a first configuration and a second configuration to secure the intraocular device to an eye; and a delivery device operable to deliver the intraocular device to the eye and manipulate the attachment mechanism to transition between the first configuration and the second configuration, wherein the delivery device is adapted to hold the intraocular device for implant and includes a shaft and a rod that rotates relative to the shaft, the rod and shaft being configured to transition the attachment mechanism between the first configuration and the second configuration during implantation of the intraocular device.

11. The system of claim 10 wherein the intraocular device comprises an intraocular pressure sensor.

12. The system of claim 10 wherein the attachment mechanism comprises a deployable portion that is manipulated by the delivery device to transition between the first configuration in which the deployable portion is compressed and the second configuration in which the deployable portion is extended to secure the intraocular device to an iris of the eye.

13. The system of claim 12 wherein the deployable portion comprises a torsional spring and a hooked end that rotates along an axis during the transition to the second configuration to thread the hooked end through the iris.

14. The system of claim 10 wherein the intraocular device and the attachment mechanism are coplanar.

15. The system of claim 10 wherein the attachment mechanism comprises a planar substrate having a first gripping portion and a second gripping portion that are manipulated by the delivery device to open to define a gap in the first configuration and close to grip a tissue within the gap in the second configuration to secure the intraocular device to the eye.

16. The system of claim 10 wherein the attachment mechanism comprises a first structure operable to be inserted into a tissue of the eye and a second structure different from the first structure that is operable to be inserted into the tissue of the eye.

17. The system of claim 16 wherein at least one of the first structure or the second structure comprises a beveled blade.

* * * * *